United States Patent
Husher et al.

(10) Patent No.: US 6,323,632 B1
(45) Date of Patent: Nov. 27, 2001

(54) SOLID STATE RF OSCILLATOR-DETECTOR FOR FLOW CYTOMETER

(75) Inventors: Frederick K. Husher, Pembroke Pines, FL (US); Gerard Schneider, Irvington, NY (US); Lazaro Ramirez, Miramar, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/374,911

(22) Filed: Aug. 13, 1999

(51) Int. Cl.[7] .............................. G01N 27/00; G01V 3/00; G01R 27/02
(52) U.S. Cl. ..................... 324/71.1; 324/71.4; 324/610; 324/316
(58) Field of Search .................. 324/71.1, 71.4, 324/610, 316

(56) References Cited

U.S. PATENT DOCUMENTS

| | | | |
|---|---|---|---|
| 3,502,974 | * 3/1970 | Coulter et al. | 324/71.1 |
| 3,898,637 | * 8/1975 | Wolstenholme | 340/606 |
| 3,931,569 | * 1/1976 | Hyde | 324/316 |
| 3,944,917 | * 3/1976 | Hogg et al. | 324/71.1 |
| 3,993,947 | * 11/1976 | Maltby et al. | 324/610 |
| 4,015,464 | * 4/1977 | Miller et al. | 73/61.75 |
| 4,298,836 | * 11/1981 | Groves et al. | 324/71.1 |
| 4,420,720 | * 12/1983 | Newton et al. | 324/71.4 |
| 4,525,666 | * 6/1985 | Groves | 324/71.1 |
| 4,710,757 | * 12/1987 | Haase | 324/71.1 |
| 4,791,355 | * 12/1988 | Coulter et al. | 324/71.1 |
| 4,924,185 | * 5/1990 | Matsutani | 324/319 |
| 5,125,737 | * 6/1992 | Rodriguez et al. | 356/39 |
| 5,832,772 | * 11/1998 | McEwan | 73/290 R |
| 6,015,386 | * 1/2000 | Kensey et al. | 600/486 |
| 6,093,186 | * 7/2000 | Globe | 606/34 |

* cited by examiner

*Primary Examiner*—Glenn W. Brown
*Assistant Examiner*—Wasseem H. Hamdan
(74) *Attorney, Agent, or Firm*—Charles E. Wands; Mitchell E. Alter

(57) ABSTRACT

A junction field effect transistor (JFET) RF oscillator-detector circuit generates an RF signal for an apparatus for conducting electrical measurements of particles contained in a carrier fluid passing through an aperture in a cytometer flow cell. The JFET oscillator includes a plurality of parallel-coupled JFETs having respectively different $V_{DS}$ vs. $I_{DS}$ characteristics, that are biased to operate at square law detection regions of their respective $V_{DS}$ vs. $I_{DS}$ characteristics. One JFET operates in Class C mode, while the other operates in Class AB mode. An RF resonant circuit is electrically coupled to the JFETs and to the measurement cell, and is operative to establish the frequency of an RF field applied to the measurement cell. An RF load change detection circuit is coupled to the RF resonator circuit and is operative to detect an RF load change associated with a modification of the RF field as a result of a particle within the measurement cell aperture.

12 Claims, 4 Drawing Sheets

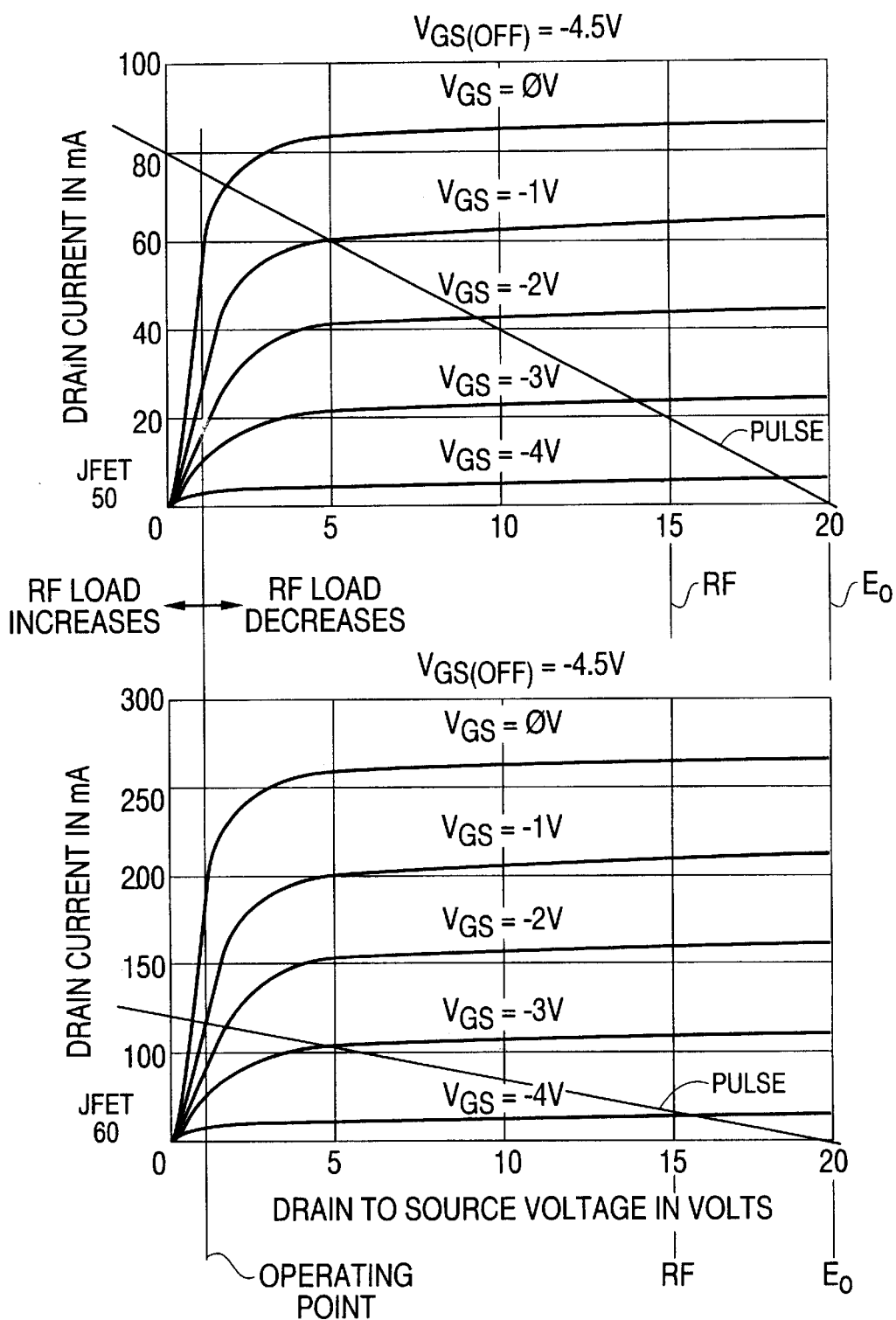

SOLID STATE RF OSCILLATOR-DETECTOR FOR FLOW CYTOMETER

FIELD OF THE INVENTION

The present invention relates in general to RF oscillator/detectors of the type that are used for conducting electrical measurements of particles (e.g., blood cells) contained in a carrier fluid in a flow cytometer system. The invention is particularly directed to a new and improved solid state RF oscillator-detector circuit, that employs a dual junction field effect transistor (JFET)-based Hartley RF oscillator, having a relatively low Q tank circuit, that is coupled to the flow cell by an impedance-matching transformer.

BACKGROUND OF THE INVENTION

As an adjunct to the diagnosis and treatment of disease, the medical industry commonly employs various types of particle flow cytometers, such as that diagrammatically illustrated at 10 in FIG. 1, to analyze particles in a patient's body fluid (e.g., blood cells). For analyzing a patient's blood, for example, a whole blood sample is initially diluted with a saline solution, lysed to explode all the red cells, and then stabilized to return the remaining white cells to their original size.

The prepared blood sample is then placed in a sample holding chamber 12, and a stream of the blood sample is conveyed along a flow channel 11 from the holding chamber 12 through a restricted orifice or aperture 14, that allows particles to be counted one at the time, and into a receiving chamber 16. Via electrodes 21 and 23 that are respectively coupled to either end of the flow cell's holding chambers (holding chamber 12 and receiving chamber 16) a DC electrical field for measuring the displaced volume of each particle and an RF field for measuring the density of each particle passing through the aperture 14 are applied to the flow cell 10 by way of an oscillator-detector circuit 17, which is preferably configured as a Hartley oscillator (although other oscillator architectures may also be used).

As particles pass through the flow cell orifice 14, they introduce changes in the resistance of the orifice in proportion to their size or volume. These changes in resistance are reflected as DC voltage pulses at the electrodes 21 and 23. The density or opacity of the blood cells is associated with changes in reactance of the flow cell aperture 14. By coupling the electrodes 21 and 23 of the flow cell 10 in parallel with the resonance (LC tank) circuit of the RF oscillator-detector circuit 17, changes in the reactance of the flow cell are reflected as a corresponding change in the operation of the RF oscillator, which is measured by means of an RF pulse detector/demodulator.

For non-limiting examples of U.S. Patent literature detailing conventional electronic tube based flow cell RF oscillator detector circuits, attention may be directed to the Coulter et al, U.S. Pat. No. 3,502,974: Groves et al, U.S. Pat. No. 4,298,836; Groves et al, U.S. Pat. No. No. 4,525,666; and Coulter et al, U.S. Pat. No. 4,791,355.

Now although a tube-based flow cell measurement circuit of the type shown in FIG. 1 is effective to provide an indication of both particle size and density, it suffers from a number of problems which are both costly and time-consuming to remedy. A fundamental shortcoming is the fact that it was originally designed as and continues to be configured using relatively old electronic tube components. This potentially impacts component availability, as the number of manufacturers of vacuum (as well as gas filled) electronic tubes continues to decline. In addition, the effective lifetime of a newly purchased and installed tube in the RF (Hartley) oscillator is not only unpredictable, but experience has shown that the effective functionality of most tubes within the Hartley oscillator—detector circuit is very limited, (even though a tube tester transconductance measurement shows a tube to be good). At best a tube can expect to last somewhere in a range of three to nine months—and typically involves on the order of two repair/maintenance service calls per year per flow cell.

SUMMARY OF THE INVENTION

While it might seem that a straightforward solution to the tube aging problem would simply involve replacing the electronic tube (e.g., triode) with a solid state device, such as a bipolar transistor, MOSFET, JFET and the like, such is not the case. Investigation by the present inventors has revealed that, in order to exhibit the sensitivity necessary to successfully function as a detector, the tube must operate over a relatively narrow, steep sloped region of its plate current versus plate voltage relationship, shown at 27 in the triode characteristic of FIG. 2.

It has been found that the relatively short mean time before failure (MTBF) of a conventional electronic tube-based flow cell measurement circuit is due to the fact that, as the tube ages, the slope of its plate current versus plate voltage characteristic at $V_{GRID}=0$ falls off quickly, and thereby degrades the tube's sensitivity to the extent that it no longer effectively functions as a detector, even though it may continue to operate as an RF oscillator.

If one considers the active device's (tube or JFET) operating range sensitivity (plate or drain voltage vs. grid or gate voltage) as a measure of transconductance (gm) dependence, from a comparison of the respective characteristic curve sets shown in FIGS. 5A (triode) and 5B (JFETs), it can be readily seen that a JFET provides a considerable improvement over a tube.

Typically, for a triode, this becomes 300 v/0.1 v=3000:1 vs. for a JFET 20 v/0.1 v=200:1. This is very important, given the small change in grid/gate voltage for a disturbance caused by the blood cell in the flow cell. Thus, an electronic tube will see a times fifteen degradation over a JFET for the same grid/gate voltage change, which makes the tube very dependent upon it's transconductance gm. A small decay in the tube's gm will then result in complete loss of detection capability. Thus, simply reconfiguring a conventional tube-based Hartley oscillator out of solid state components will not necessarily solve the problem.

In accordance with the present invention, the discovery of the above-discussed sensitivity-dependent slope limitation requirement has led the present inventors to design a new and improved solid state-based Hartley oscillator-configured flow cell detection circuit, that not only solves the tube-aging problem, but provides substantially improved performance. As will be described, the oscillator-detection circuit of the invention employs a pair of JFETs as its principal active devices (respectively operating in Class C and Class AB mode), which enables the circuit to achieve near zero noise operation with a very high $V_{DS}$ vs. $I_{DS}$ slope at a $V_{GS}=0$ volts.

Advantageously, JFETs are inherently noiseless, except for the thermal noise intrinsic with channel resistance between the drain and the source. In the operation of the oscillator/detector, it is very easy to be misled as to the value of rms noise level seen at the detector output. The circuit noise that is coupled to the detector output is primarily related to the conduction time of JFET channel resistance.

The shorter conduction time, reduction of channel resistance, or reduction of channel current, the lower the effective noise.

As will be described, operation with two JFETs in different class modes helps reduce the noise floor. A low current in the Class AB JFET stage in combination with low channel resistance allow for a lower noise floor. When the Class C JFET stage switches on, then only for that time is the additional channel device a noise source. The tradeoff is conduction time vs. the product of conduction current and conduction resistance.

In accordance with a preferred embodiment of the invention, a pair of parallel-coupled JFETs having different transfer functions, in particular different pinchoff $V_{GS}$ and max $I_{DSS}$ characteristics, are employed as the principal active element of the RF oscillator. As pointed out briefly above, there are two modes of operation that occur in both a JFET and a triode tube, as shown in FIGS. 5A and 5B, respectively. As far as RF mode operation is concerned, both devices are operated in their linear saturated regions with the RF load lines.

However, for the detection process, both devices operate in their square-law regions, as shown in the pulse load line. This is not intuitively evident from a circuit simulation, as only the RF region is operative and the simulation models do not include the square-law region. Operation in the saturation region cannot develop any detectable change due to a perturbation in the loading by a cell. The detection process operates near Vgs=0 v and Vgc=0 v, where the highest slope in the square-law region occurs. Both circuits are biased for the saturated region to support RF generation.

There has been considerable study on the temperature effects of the JFET to detection stability. A single JFET device can be biased such that it can be made substantially independent to effects of temperature. However, this biasing condition causes the JFET to be operated, such that Vgs is quite far away from Vgs=0 v. The net result is that the oscillator will not function as a detector. While it is possible to cause the biasing to change as a result of temperature—which stabilizes the JFET—the net result is that the correction activity introduces a noise source, that limits its usefulness.

With a pair of JFETs operating with different parameters, each device will be set at a different temperature, which leads to problems with temperature stability. While it may be possible to selected two JFET devices such that they will cancel out each other's temperature curves, this is not a viable solution from a manufacturing perspective. As a result, it is preferred to install the two JFETs and an associated current mirror in a temperature control chamber. This provides the circuit designer with considerable latitude in the choice of JFETs, as only the detection process needs to be considered.

In a preferred embodiment of the invention, the respective parallel-connected source-drain paths of the two (Class C, Class AB) JFETs are coupled between a DC voltage supply node and a center tap of a primary winding of a flow cell impedance-matching, ferrite core toroid transformer. This transformer also forms an inductive component portion of a relatively low Q resonator circuit that sets the fundamental resonant RF frequency of the oscillator. The frequency of the low Q tank circuit can be adjusted by a variable capacitor.

The transformer's primary winding is coupled to parallel connected gates of the JFETs through a gate input circuit, that includes a DC battery (resistor-capacitor) path for increasing gain as a bootstrap impedance feedback at low frequencies, and a parallel capacitor path that effectively bypasses the battery at RF frequencies.

The transformer allows the required gate biasing resistance to be matched to the load presented by the flowcell. By matching to the flow cell load is meant that the low Q tank circuit's transformer is power-matching the RF oscillator to the flow cell for optimum detection sensitivity. This is not meant to imply that the impedance of the flow cell is being matched to that of the RF oscillator. In a tube-based circuit of the prior art, the grid bias resistance can be very high, for example on the order of one megohm, which allows two things to occur. First, the grid bias resistance has no loading impact on the tank circuit. Secondly, the tank circuit can have a very high Q (e.g., on the order of 120).

Using a transformer to enable a relatively low gate resistance to bias the JFET requires two parameters from the tank circuit: the tank Q must be low (e.g., between 8 and 20), as gate resistance dominates the loading, and a step-up secondary winding provides matching between the lower impedance of the JFETs and the higher impedance of the flow cell. In addition, the RF voltage applied across the flow cell can be considerably higher than could be tolerated by the JFETs directly.

More particularly, the RF voltage presented across the flow cell itself is approximately what is seen at the JFETs gates. However, an AC voltage divider is formed between the transformer secondary winding and the flow cell with a capacitor. The capacitor forms part of the impedance matching between the flow cell, a coaxial feed to the flow cell, and the RF oscillator. Since a DC current is also presented to the flow cell to measure the volumetric displacement of a particle, the secondary winding of the transformer is AC-coupled to the flow cell. The capacitor serves to match the Rf oscillator to the flow cell and its coaxial feed, while blocking the DC current of the volumetric measurement. Within reason, the higher the applied RF voltage across the flow cell, the more sensitive the RF oscillator/detector becomes to a dielectric impedance change caused by the presence of a particle (blood cell) in the detection aperture.

The primary winding of the low Q tank circuit's transformer is further coupled to a current sink compliance voltage load sensing node of a current (sink) mirror circuit. The current mirror circuit is operative to cause the RF oscillator to function as a load detector, by multiplying current variations by a synthetic high resistance, and is configured to maintain a constant output impedance throughout changes in compliance voltage. To optimize its functionality, the slope of the collector current vs. base voltage characteristics of its two bipolar transistors is relatively shallow, so that with load changes the output impedance will remain effectively constant and high.

The current mirror is coupled to a bypass capacitor which provides both a low impedance path to ground for the RF signal, and serves as an energy storage device for ensuring a good transient response for the current mirror circuit. The bypass capacitor serves to capture a change in RF oscillator load due to a particle passing through the flow cell aperture. The value of the bypass capacitor is chosen to match the RF impedance seen looking into the tank transformer. Thus, the value of the capacitor will have the same RF impedance as that of the tank winding. This matching of the RF impedances will yield the maximum detected load change signal.

As pointed out above, the RF oscillator employs both a Class C JFET and a Class AB JFET. For optimum operation in Class C the conduction angle is 153 degrees. Class AB causes the conduction angle to be increased to a value between 200 and 300 degrees. Since there is no steady state conduction of either JFET, the JFETs may be considered to be operating as current pumps rather than as linear devices. Each JFET injects a current pulse simultaneously with the cyclic swing of the tank circuit. The Class AB JFET has a higher pinchoff voltage and lower max Idss than the Class C JFET. As a consequence, the Class AB JFET injects a smaller current pulse but of longer duration into the tank circuit than the Class C JFET.

The Class C JFET injects a power pulse that rapidly ramps up the gain of the loop much higher than the other JFET could achieve. Since noise is a function of current and time into an impedance, then if the power pulse is shorter than the average, the amount of noise energy is reduced. What is effectively achieved is a tradeoff between that required to sustain operation as an RF oscillator and what is required to function as a load change detector. The change in pulse current is coupled to downstream amplification circuitry.

In operation, a DC current source delivers a prescribed current coupled by the flow cell interface circuit to a flow cell electrode, to produce a DC electrical field for measuring the size of each particle passing through the flow cell's detection aperture. A disturbance in this DC electric field due to a particle is reflected by a change in compliance voltage of the current source. When particle size within the aperture increases, the aperture resistance will also increase, increasing the current source compliance voltage, as the RF oscillator requires less current pulse injection to maintain RF amplitude. To detect a change in particle opacity or density, the nominal RF frequency is coupled by the transformer secondary through the interface circuit to the flow cell. The presence of a particle in the flow cell aperture causes a change in flow cell reactance, as the resistance and capacitance of the aperture are effectively part of the resonant circuit.

Although the Q of the transformer-configured tank circuit will increase slightly due to the presence of a particle in the aperture, this does not have nearly the impact on the JFET oscillator's operation as in a tube design. In a high Q tank circuit, the presence of a particle causes the oscillator's frequency to shift upwards towards the Q peak of the tank. The closer the oscillator frequency approaches that of the Q peak, the less pulse injection current is required to maintain the oscillator's voltage amplitude.

For the case of a low Q tank, there is little change in frequency due to the presence of the particle, as there is no significant tank resonance frequency. Still, there will be a reduction in loading and the JFET will need to inject less of a current pulse into the tank, to maintain the oscillator's amplitude. As a consequence, a low Q tank design responds almost exclusively to the real resistance change caused by the loading of a particle. A high Q tank, however, is very sensitive to both the real and reactive load changes, as the reactive change causes significant changes in the oscillator's frequency. This is an important issue as the dual JFET detector of the invention responds only to the power loading changes caused by a particle, which results in better small particle linearity. This improvement in linearity is seen mostly in particles that are smaller than five microns in diameter.

BRIEF DESCRIPTION OF THE DRAWINGS

FIG. 5B shows a pair of drain current vs. drain-to-source voltage characteristics of respectively different JFETs and associated load lines.

DETAILED DESCRIPTION

Figure 1:
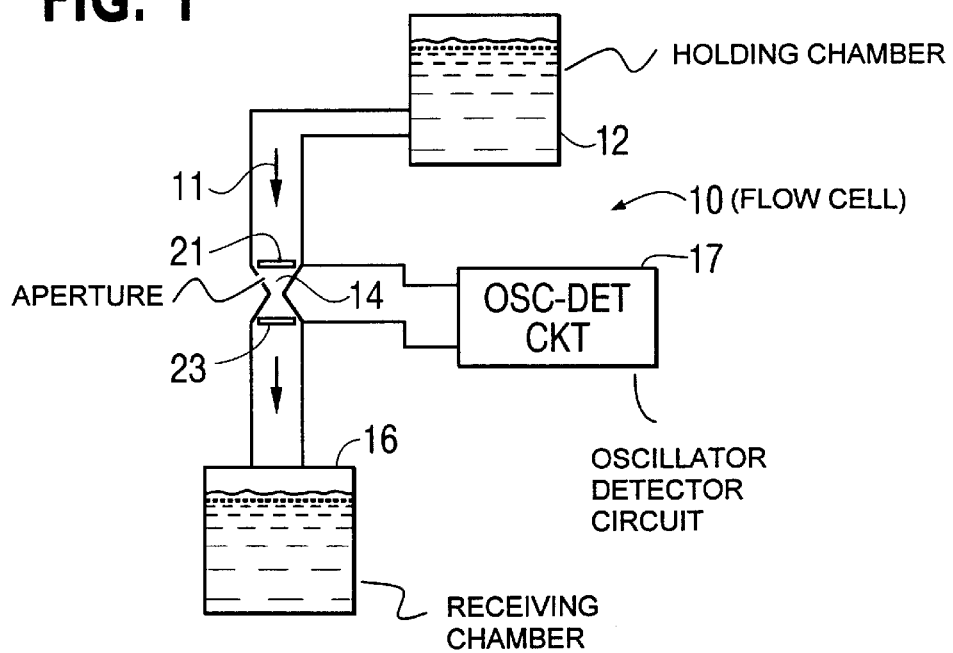
FIG. 1 diagrammatically illustrates a particle flow cytometer.
Figure 2:
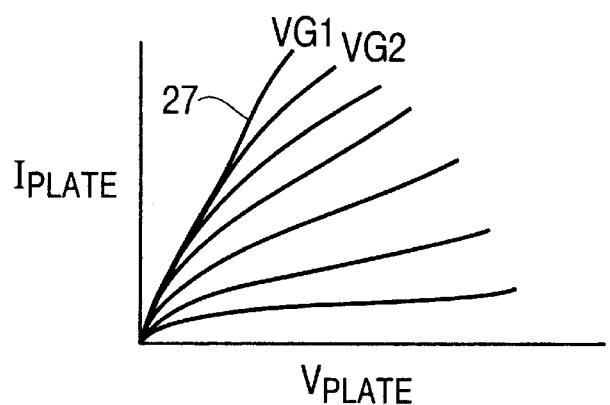
FIG. 2 shows the plate current versus plate voltage characteristic of a vacuum triode tube employed in a conventional flow cell measurement circuit.
Figure 3:
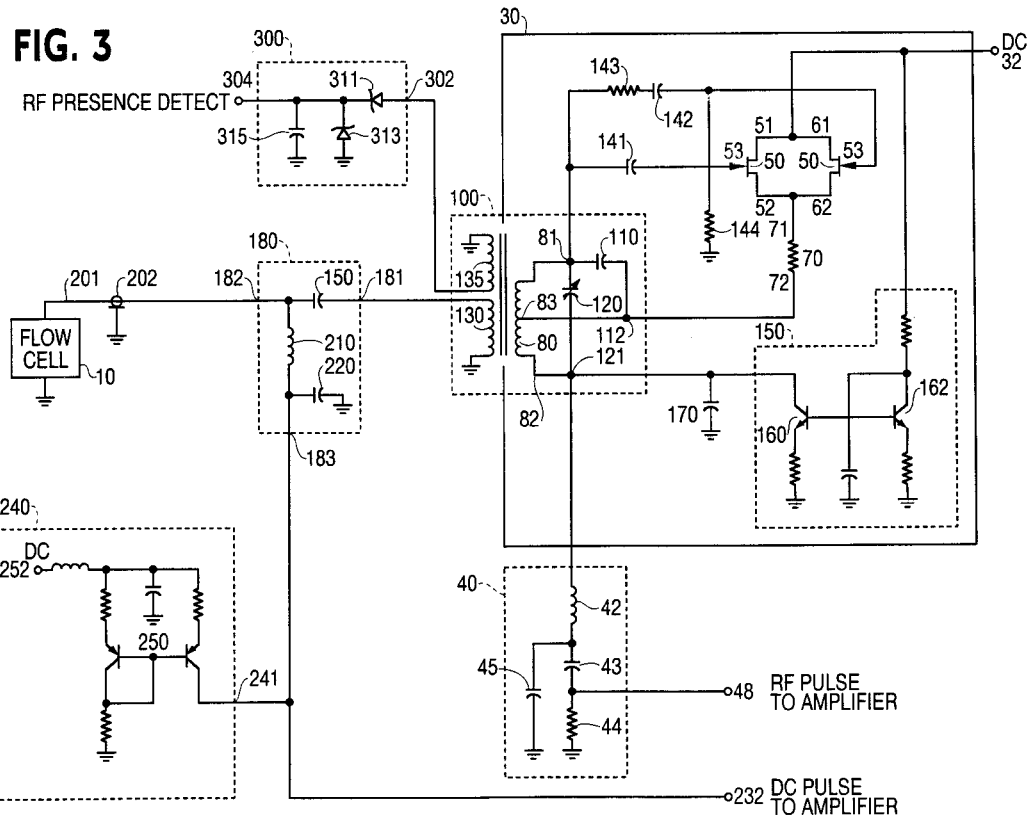
FIG. 3 is a schematic diagram of a dual JFET-based oscillator-detector for a flow cell measurement circuit in accordance with the present invention.

Referring now to FIG. 3, an embodiment of a dual JFET-based oscillator-detector for use in a flow cell measurement circuit in accordance with an embodiment of the present invention is schematically illustrated as comprising a solid state RF oscillator 30, that is coupled through an interface circuit 180 to a flow cell, such as a blood flow cell, shown at 10.

Figure 5A:
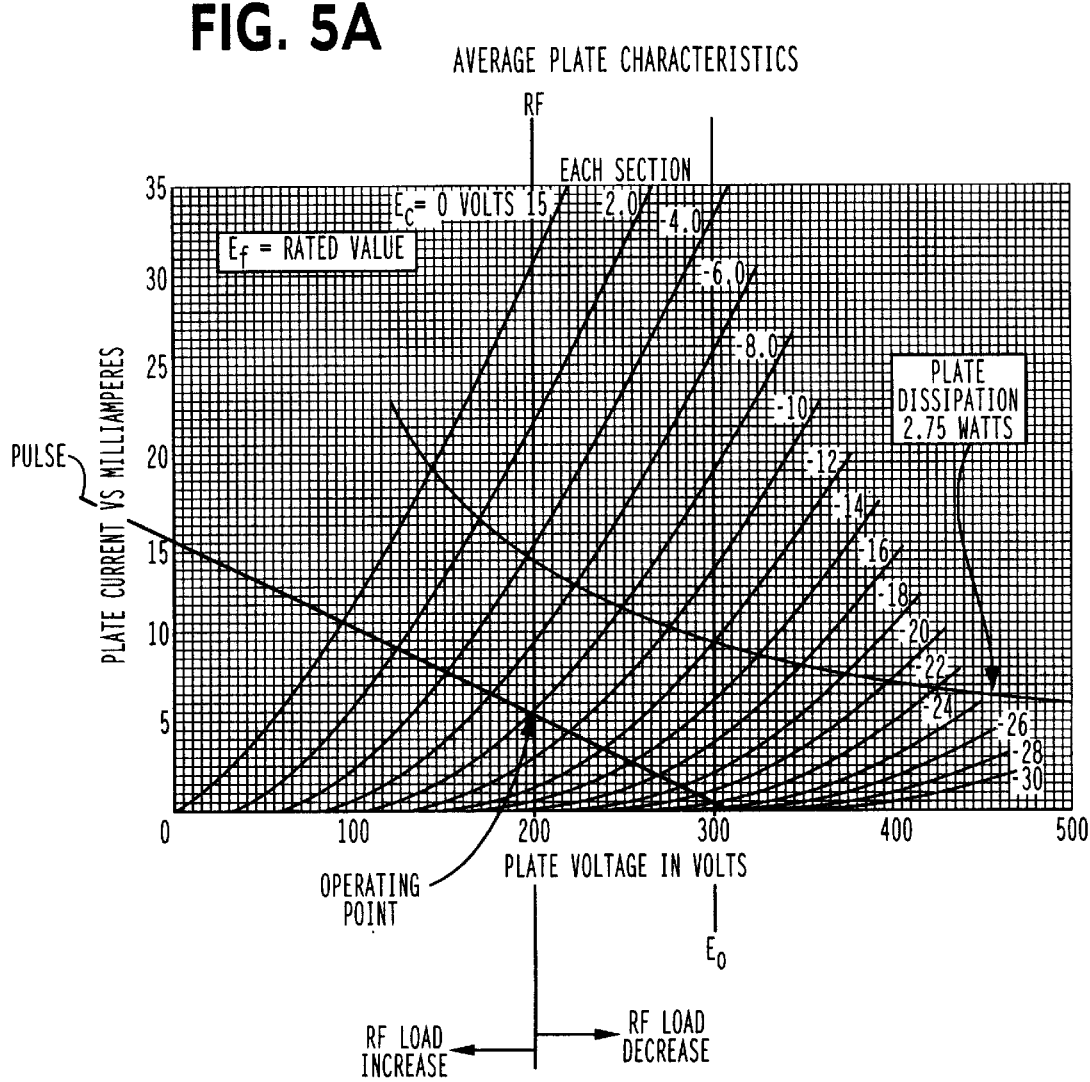
FIG. 5A shows a load line superimposed on a plate current versus plate voltage characteristic of a vacuum triode tube.

In accordance with a preferred embodiment, a pair of parallel-coupled JFETs 50 and 60 having respectively different transfer functions, in particular different pinchoff $V_{GS}$ and max $I_{DSS}$ characteristics, such as those shown in FIG. 5B, are employed as the principal active elements of the RF oscillator 30. As described briefly above, there are two modes of operation for these two JFETs. For RF mode, the two JFETs 50 and 60 are operated in their linear saturated regions with their RF load lines of FIG. 5B. For particle detection, they are operated in their square-law regions, as shown by the pulse load lines, as operation in their saturation regions cannot develop a detectable change due to a perturbation in the loading by a particle. The detection process operates near Vgs=0 v and Vgc=0 v, as this is where the highest slope in the square-law region occurs. The load change is observed as the average in the compliance voltage across a by-pass capacitor 170 of a current (sink) mirror circuit 150.

A first JFET (e.g., JFET 50) operates in Class C mode, while a second JFET (JFET 60) operates in Class AB mode. This is readily achieved by selecting JFET 50 to have a first $V_{GS}$ (e.g., $V_{GS50}$=2V), and selecting JFET 60 to have a second $V_{GS}$ (e.g., $V_{GS60}$=4V). The net effect is a slope change in the composite $V_{DS}$ vs. $I_{DS}$ characteristic when the class C device (e.g., JFET 60) turns on (when $V_{GS}$ reaches 4 v).

The use of a pair of parallel-connected JFETs also increases the current handling capability of the RF oscillator-detector. As a non-limiting example, low voltage JFETs operating in a $V_{GS}$ range of (−1 to −7) volts, such as J111 Series JFETS from TEMIC Semiconductor, or 2N6550 JFETS from InterFET may be employed.

As noted earlier, while one might choose the values of $V_{GS}$ and $I_{DS}$ for the two JFETs 50 and 60, so that there is no change in detected particle size vs. output signal for a variation in temperature, such a task is relatively impractical, particularly from a standpoint of attempting to balance three terms for each JFET: $V_{GS}$, $I_{DS}$ and device temperature. As pointed out above, to circumvent this problem, the JFETS 50 and 60 and an associated current (sink) mirror circuit 150 are preferably enclosed in a temperature controlled housing or chamber. A temperature controlled environment provides the circuit designer with considerable freedom to choose JFET characteristics that provide the intended detector performance. In effect, essentially any two JFETs having $V_{GS}$ values more than two volts apart can be used. The remaining design parameter is oscillator current for maximum detector sensitivity.

The respective parallel source-drain paths 51–52 and 61–62 of JFETs 50 and 60 are coupled between a DC voltage supply node 32 and a first end 71 of a bias resistor 70, a second end 72 of which is coupled to a center tap node 83 of a primary winding 80 of a multiple winding transformer 90. The transformer 90 is preferably of a ferrite core based, toroidal winding configuration and is used to step the voltage swing of the RF oscillation voltage up to the flow cell load and increase the load impedance seen by the flow cell, namely matching the impedance of the flow cell with that of the oscillator. In addition, the transformer forms an inductive component portion of a relatively low Q LC tank or resonator circuit shown in dotted lines 100, that sets the fundamental resonant frequency of the RF oscillator 30.

It should be noted that the use of a multiple winding transformer also involves the following considerations. For a transformer having only two windings, three resonant frequencies are possible: 1—primary with the addition of the secondary capacitance; 2—secondary with the addition of the primary capacitance; and 3—primary with the addition of mutual capacitance. Where additional windings are involved, there is an increase in the number of possible resonant frequencies.

It is important to ensure that the RF oscillator cannot readily hop to another resonant point in response to a change in oscillator loading. A relatively expeditious way to evaluate this possibility is to use a gain/phase analyzer, wherein a phase vs. frequency plot indicates all of the resonant frequencies that the transformer will support. If any of these resonant frequencies are too close together, the RF oscillator may hop to another resonant point in response to a loading change. When this happens a hysteresis loop is formed, whereby the hop frequencies between the two resonant points require an overshoot to occur before the transition state can occur.

As noted above, since LC tank circuit 100 has a low Q, it has little sensitivity to reactance changes in the flow cell, as there is insignificant change in frequency. Therefore, the tank 100 responds almost exclusively to the real resistance change caused by the loading of a particle. This contributes to JFET detector 30 responding only to resistance loading changes caused by the particle, resulting in better small particle linearity.

A first end node 81 of primary winding 80 is coupled to first end 11 of a fixed value capacitor 110. A second end 112 capacitor 110 is coupled to the center tap node 83 of primary winding 80. The end node 82 serves as a current sink compliance voltage load sensing node of a current mirror circuit 150, and is coupled to a first end 121 of a variable capacitor 120. A second end 122 of capacitor 120 is coupled to end node 81 of primary winding 80. The average DC voltage at node 82 reflects a change in loading of the RF ocilator by a particle.

The combined capacitance of capacitors 110 and 120 and the inductance of the primary winding 80 and a secondary winding 130 of the tank/resonator circuit 100 are selected to establish the resonant frequency of the oscillator, for example, in a range of from 10–40 MHz, as a non-limiting example. The value of the capacitor 110 is preferably selected to stabilize the frequency of operation of the RF oscillator 30 (prevent hopping between resonant frequencies associated with the two transformer windings, as described). The use of variable capacitor 120 allows the resonant frequency to be 'tuned' as desired within the available range defined by the parameters of the tank circuit's LC components.

The ability to adjust the frequency of the RF oscillator without impacting detector sensitivity and operation facilitates tuning out unwanted frequency spurs, such as might be generated by a local radio station, for example. In accordance with a non-limiting but preferred embodiment, variable tuning capacitor 120 may comprise a glass piston tuning capacitor. This type of capacitor serves to prevent changes in capacitor value as a result of changes in atmospheric pressure, and thereby eliminates the issue of manufacturing the circuit at sea level for use at an elevated altitude.

The first end node 81 of the primary winding 80 is further coupled to the parallel connected gates 53 and 63 of JFETs 50 and 60, through a gate input circuit 140. The gate input circuit 140 has a first path comprised of a capacitor 141, and a second path containing series-connected capacitor 142 and resistor 143 coupled in parallel with capacitor 141. The series connection second path through capacitor 142 and resistor 143 acts as a DC battery input to the gates of the JFETs 50 and 60, and also increases the gain as a bootstrap impedance feedback at low frequencies, while the first path through capacitor 141 effectively bypasses the battery at RF frequencies.

A further gate bias resistor 144 is coupled between gates 53 and 63 and a reference potential terminal (ground). The values of the resistors 70 and 144 may be selected to set the particle detection sensitivity of the circuit. The action of the transformer 80 allows the gate bias resistor 144 to be low, without significantly loading the flow cell.

The second end node 82 of the primary winding 80 is further coupled to a low-pass filter 40. Low-pass filter 40 is operative to reject the RF signal seen on a by-pass capacitor 170 within oscillator 30. The current mirror circuit 150 is operative to cause the oscillator 30 to function as a load detector, by multiplying current variations by a synthetic high resistance (which is equivalent to using a high voltage supply and a plate load resistor in a conventional triode tube configuration). The current mirror circuit 150 is configured to maintain a constant output impedance throughout changes in compliance voltage.

In order to optimize the functionality of the current mirror 150, the slope of the collector current vs. base voltage characteristics of the two bipolar transistors 160 and 162 should be relatively shallow, so that with load changes the output impedance will remain effectively constant and high. The collector 161 of the transistor 160 is coupled to the second end node 82 of the primary winding 80 and to a capacitor 170, which provides both a low impedance path to ground for the RF signal, and serves as an energy storage device for ensuring a good transient response for the current mirror circuit 150.

Capacitor 170 serves to capture a change in RF oscillator load due to a particle passing through the flow cell aperture. As the load changes as a result of the presence of a particle in the flow cell aperture, the compliance voltage of the current mirror 150 will change. The values of the bypass capacitor 170 and the components of the current mirror 150 are preferably selected to maximize the magnitude of the detected RF pulse, which is sensed at the node 82, as noted above.

Because the RF oscillator employs both a Class C JFET and a Class AB JFET, the current demand at the node 82 as seen by the current mirror will have only a pulse component. The change in pulse current is averaged across the capacitor 170 and low frequency AC coupled to downstream amplification circuitry through low-pass filter circuit 40. The low-pass filter circuit 40 includes a series circuit of an inductor 42—capacitor 43—resistor 44 coupled to ground, with the node 45 between inductor 42 and capacitor 43 coupled to grounded capacitor 46. The load-induced compliance voltage, such as that associated with a particle detected in the flow cell orifice, is extracted via an RF pulse output terminal 48 coupled to the node 47 between capacitor 43 and resistor 44. The RF output terminal 48 is ported to downstream RF pulse amplification circuitry (not shown).

As pointed out above, in addition to providing an inductive component portion of the relatively low-Q, LC tank or resonator circuit 100, the transformer 90 is used to match the impedance of the flow cell with that of the RF oscillator 30. For this purpose transformer 90 has its secondary (toroidal) winding 130 coupled between a first port 181 of a flow cell interface circuit 180 and ground.

The secondary winding 130 is preferably (minimal spacing) interleaved with and wound upon the same toroid core in the same winding direction as the primary winding 80 of the transformer 90, so as to provide a high coupling coefficient between the transformer windings. Also, the turns ratio between the primary and secondary windings is defined in accordance with the impedance parameters of the oscillator and flow cell. As a non-limiting example the ratio of turns of the primary winding 80 to the secondary winding 130 may be 2:1.

The flow cell interface circuit 180 is configured to couple DC and RF to and from the flow cell, while also decoupling the DC voltage from the RF signal. For this purpose, the flow cell interface circuit 180 comprises a first capacitor 190 that is coupled between the first port 181 and a second port 182. The first capacitor 190 of the interface circuit 180 serves as a short circuit for RF signals, while blocking DC.

An additional feature of the transformer design of the present invention is that the ferrite material used will not support low frequency signals; thus, any residual low frequency signals coupled through the series coupling capacitor 190 cannot pass through to the gates of the JFETs. Port 182 may be coupled to the flow cell by means of a section of transmission line, such as the center conductor 201 of a section of coaxial cable, the outer sheath 202 of which is coupled to ground.

Advantageously, the use of the coupling transformer 90 to match the impedance of the flow cell to that of the RF oscillator avoids the complexity of having to precisely set the parameters of a transmission line that could otherwise be used to connect the tank circuit to the flow cell.

An inductor 210 is coupled between the second port 182 and a third port 183, and is employed to provide a low frequency or DC coupling and high frequency (RF-blocked) path between ports 182 and 183. The flow cell interface circuit 180 further includes a second capacitor 220, which is coupled between the third port 183 and a fourth port 184, which is coupled to ground. Like the first capacitor 190, the second capacitor 220 serves as a short circuit for RF signals, while blocking DC. The interface circuit's third port 183 is coupled via a link 230 to a DC current source 240, that contains a current mirror circuit 250 coupled between a DC power supply terminal 252 and a current supply port 241. Link 230 is further coupled to a DC response output port 232, that is ported to downstream DC pulse amplification circuitry (not shown).

In order to provide an indication that the oscillator is in fact operating, the transformer 90 further includes a tickler transformer winding 135 that is coupled to an input port 302 of an RF oscillation detector 300. RF oscillation detector 300 is comprised of a Zener diode 311 coupled in circuit between input port 302 and output port 301. A further Zener diode 313 and a capacitor 315 are coupled in parallel between port 301 and ground. Due to the fact that the ferrite core of transformer 90 is not functional at low frequencies, there is no low frequency noise path from the RF oscillation detector 300 into the oscillator 30. Also, a high level AC voltage can be realized from only a few turns of the tickler winding 135, facilitating rectification of the signal to a DC level by the relatively simple circuit arrangement as shown.

In operation, the current source 240 provides a prescribed DC current via port 241, which is coupled over link 230 to the third port 183 of the flow cell interface circuit 180. Via inductor 210, the compliance voltage is coupled to the second port 182 and via coaxial cable 200 to one of the electrodes of the flow cell (the other electrode of which is grounded). The applied compliance voltage is blocked from port 181 due to the presence of capacitor 190.

As pointed out above, the compliance voltage is used to generate a DC electrical field for measuring the size of each particle passing through the orifice aperture of the flow cell. A perturbation in this DC electric field as a result of a change in resistance due to the presence of a particle is reflected by a change in the compliance voltage on link 230, with the magnitude of the change being indicative of the volume or size of the particle. This particle size-representative DC pulse is applied to output port 232 for processing by downstream circuitry, as described.

To detect a change in particle opacity or density, the nominal RF frequency (e.g., a 10–40 MHz signal, referenced above) generated by the RF oscillator 30 is coupled via the secondary winding 130 of the transformer 90 to the first port 181 of flow cell interface circuit 180. This RF signal is coupled via capacitor 190 to the second port 182 and applied via the coaxial cable 200 to one of the electrodes of the flow cell. The applied RF signal is blocked from port 183 due to the presence of inductor 210.

The RF frequency produces an RF field for measuring the opacity or density of each particle passing through the orifice aperture of the flow cell. The presence of a particle in the flow cell aperture produces a change in reactance in the flow cell, as the resistance and capacitance of the flow cell aperture are effectively part of the resonant circuit.

As noted earlier, even through the Q of the tank circuit 100 will increase slightly due to the presence of a particle in the aperture, this does not have nearly the impact on the JFET oscillator's operation as in a conventional high Q tank tube design, in which a particle causes the oscillator's frequency to shift upwards towards the Q peak of the tank. The closer the oscillator frequency approaches that of the Q peak, the less pulse injection current is required to maintain the oscillator's voltage amplitude.

In the low Q tank circuit of the invention, there is little change in frequency due to the presence of the particle, as there is no significant tank resonance frequency. However, the reduction in loading will still be seen and the JFETs will inject less of a current pulse into the tank circuit, to maintain the RF oscillator's amplitude. Namely, the low Q tank circuit of the invention responds almost exclusively to real resistance change caused by the loading of the particle, in contrast to a high Q tank, that is sensitive to both the real and reactive load changes, as the reactive change causes significant changes in the oscillator's frequency. Thus, the JFET detector of the invention responds only to the resistance loading changes caused by the particle, which results in better small particle linearity, which is seen mostly in particles of a diameter less than five microns. As described above, a change in the value of flow cell resistance will change the amplitude of the detected RF signal; and an increase in the value of the flow cell resistance will cause an increase in the oscillator's current sink compliance voltage. There will be no change in RF envelope amplitude. It may be noted that a change in the RF carrier envelope is not modulation but a baseline shift, as modulation requires a frequency or amplitude change, which a baseline shift is not. However, Class C mode JFET causes its gate-source to act as a rectifier, so that there may be some degree of modulation or waveform distortion that occurs on every particle of the carrier. This form of waveform distortion is not considered to be modulation that is induced by the presence of a particle in the flow cell.

Figure 4:
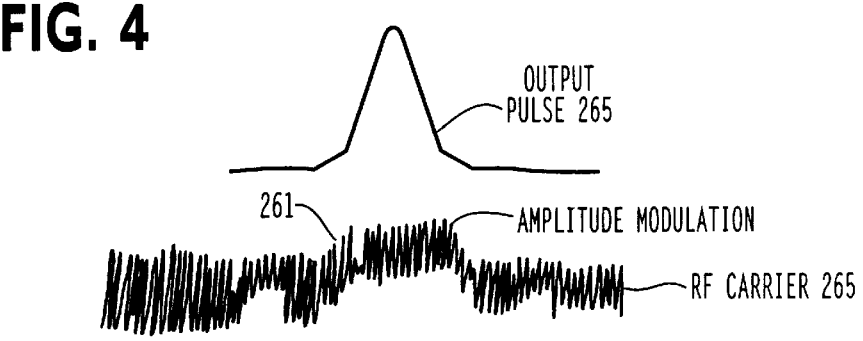
FIG. 4 shows an RF pulse waveform associated with the RF oscillator-detector circuit of FIG. 3.

An increase in the RF pulse waveform in FIG. 4, shown as an increase 261 in the amplitude of the RF current signal 263, is filtered by the low-pass filter 40 and output therefrom as RF pulse 265 via the RF pulse output terminal 48 and ported to downstream RF pulse amplification circuitry. As pointed out above, due to the low Q of its tank circuit 100, the RF oscillator 30 operates principally on the real load change in the flow cell. In contrast with a tube-based oscillator circuit, frequency shift is essentially negligible, so that the detector of the invention is effectively independent of the operating frequency of the oscillator.

The duration of the modulation of the RF current is equal to the length of time that the particle is present within the flow cell aperture. The peak of the RF signal can be utilized to differentiate between different particles that introduce different impedance changes to the flow cell.

As will be appreciated from the foregoing description, the shortcomings of a conventional tube-based flow cell measurement circuit described above are effectively obviated by the solid state-based Hartley oscillator-configured flow cell detection circuit of the invention, that not only solves the tube-aging problem, but provides substantially improved performance. By configuring the RF oscillator from a pair of parallel-coupled JFETs having respectively different $V_{DS}$ vs. $I_{DS}$ characteristics, one of which operates in Class AB and the other of which operates in Class C mode, the invention is able achieve near zero noise operation with a very high $V_{DS}$ vs. $I_{DS}$ slope at a $V_{GS}=0$ volts. Using a transformer as part of the low Q tank circuit not only provides the inductive component of the resonator, but matches the impedance of the load cell to the resonator. The inclusion of the current mirror within the RF oscillator causes the RF oscillator to function as a load detector, by multiplying current variations by a synthetic high resistance, and maintains a constant output impedance throughout changes in compliance voltage.

While we have shown and described an embodiment in accordance with the present invention, it is to be understood that the same is not limited thereto but is susceptible to numerous changes and modifications as are known to a person skilled in the art, and we therefore do not wish to be limited to the details shown and described herein, but intend to cover all such changes and modifications as are obvious to one of ordinary skill in the art.

What is claimed is:

1. A circuit wherein said RF oscillator-detector comprises a junction field effect transistor (JFET)-based RF oscillator, that includes a plurality of parallel-coupled JFETs having respectively different $V_{DS}$ vs. $I_{DS}$ characteristics, with a first JFET of said plurality of JFETs operating in Class C mode, and a second JFET of said plurality of JFETs operating in Class AB mode.

2. A junction field effect transistor (JFET) RF oscillator-detector circuit for use in an apparatus for conducting electrical measurements of particles contained in a carrier fluid passing through an aperture in a measurement cell to which an electric field is applied, said JFET RF oscillator comprising:

a plurality of parallel-coupled JFETs having respectively different $V_{DS}$ vs. $I_{DS}$ characteristics, and being biased to operate at square law detection regions of their respective $V_{DS}$ vs. $I_{DS}$ characteristics, a first JFET of said plurality of JFETs operating in a first class mode, and a second JFET of said plurality of JFETs operating in second class mode different from said first class mode;

an RF resonant circuit electrically coupled to said plurality of parallel-coupled JFETs and to said measurement cell, and establishing the frequency of an RF field applied to said measurement cell; and an RF load change detection circuit coupled to said RF resonator circuit and being operative to detect an RF load change associated with a modification of said RF field as a result of a particle within said measurement cell aperture.

3. A JFET RF oscillator-detector circuit according to claim 2, wherein said RF resonant circuit comprises a low Q RF resonant circuit containing a transformer that is operative to step up an RF voltage variation output of said RF oscillator-detector to an elevated RF voltage variation applied to said measurement cell, and increase the electrical impedance of said RF oscillator-detector seen by said measurement cell.

4. A JFET RF oscillator-detector circuit according to claim 3, further including a current mirror coupled to an RF load sensing node of said RF load change detection circuit and being operative to maintain a constant output impedance over changes in compliance voltage.

5. A JFET RF oscillator-detector circuit according to claim 3, wherein said transformer includes a tickler transformer winding coupled to an RF oscillation detector for providing an indication of the operational state of said JFET RF oscillator.

6. A JFET RF oscillator-detector circuit according to claim 4, further including a bypass capacitor coupled to said RF load sensing node, and wherein parameters of said bypass capacitor and said current mirror are selected to maximize the magnitude of an RF pulse at said RF load sensing node.

7. A JFET RF oscillator-detector circuit according to claim 6, wherein said low Q RF resonant circuit includes a glass piston variable tuning capacitor coupled with a winding of said transformer for establishing the resonant frequency of said RF resonant circuit.

8. A JFET RF oscillator-detector circuit according to claim 2, wherein said first JFET operates in Class C mode, and said second JFET operates in Class AB mode.

9. A JFET RF oscillator-detector circuit according to claim 2, wherein said measurement cell includes electrodes on input and output sides of said aperture, and further including an interface circuit that is operative to couple a DC voltage from a DC voltage source, and an RF voltage from said RF resonator circuit to said electrodes of said measurement cell, and to derive changes in said DC voltage and said RF voltage, while decoupling said DC voltage from said RF voltage.

10. For use in an apparatus for conducting electrical measurements of particles contained in a carrier fluid passing through an aperture in a measurement cell to which an electric field is applied, a method of coupling an RF field to said measurement cell and deriving changes in said RF electric field associated with the presence of a particle within said measurement cell aperture, said method comprising the steps of:

(a) providing an RF oscillator that includes a plurality of parallel-coupled JFETs having respectively different $V_{DS}$ vs. $I_{DS}$ characteristics, and biased to operate at square law detection regions of their respective $V_{DS}$ vs. $I_{DS}$ characteristics, with a first JFET of said plurality of JFETs operating in a first class mode, and a second JFET of said plurality of JFETs operating in second class mode different from said first class mode, and an RF resonant circuit electrically coupled between said plurality of parallel-coupled JFETs and to said measurement cell, and being operative to establish the frequency of an RF field applied to said measurement cell; and (b) coupling said RF resonator circuit to an RF load detection circuit that is operative to detect an RF load change associated with a modification of said RF field as a result of said presence of a particle within said measurement cell aperture.

11. A method according to claim 10, wherein said RF resonant circuit comprises a transformer that is operative to step up an RF voltage variation output of said RF oscillator-detector to an elevated RF voltage variation applied to said measurement cell, and increase the electrical impedance of said RF oscillator-detector seen by said measurement cell, and wherein step (b) comprises coupling a current mirror to an RF load sensing node of said RF load detection circuit, said current mirror being operative to maintain a constant output impedance over changes in compliance voltage.

12. A method according to claim 11, wherein said transformer includes a tickler transformer winding coupled to an RF oscillation detector for providing an indication of the operational state of said RF oscillator.

* * * * *